Figure 1:
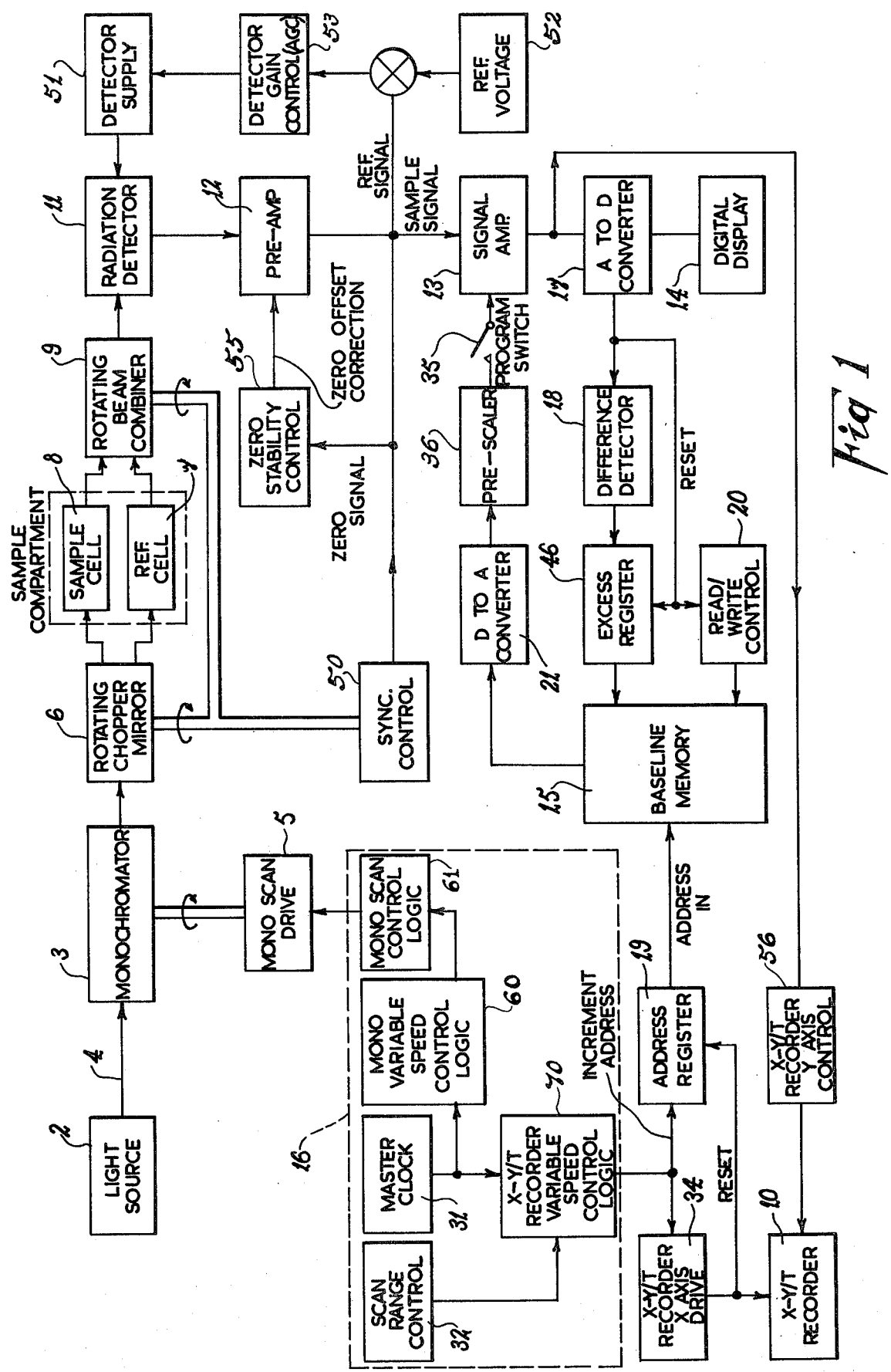

United States Patent [19]

Wildy et al.

[11] 4,171,913
[45] Oct. 23, 1979

[54] SPECTROPHOTOMETER

[75] Inventors: Peter C. Wildy, Belgrave; Ronald N. Jones, Lindfield, both of Australia

[73] Assignee: Varian Techtron Proprietary Limited, Mulgrave, Australia

[21] Appl. No.: 810,823

[22] Filed: Jun. 27, 1977

Related U.S. Application Data

[63] Continuation of Ser. No. 626,599, Oct. 28, 1975, abandoned, which is a continuation-in-part of Ser. No. 424,400, Dec. 13, 1973, abandoned, and Ser. No. 594,902, Jul. 10, 1975, abandoned.

[30] Foreign Application Priority Data

Dec. 20, 1972 [AU] Australia ............... PB1691

[51] Int. Cl.$^2$ .................................. G01J 3/42
[52] U.S. Cl. ........................... 356/325; 364/498
[58] Field of Search ............ 356/88, 89, 93–97, 356/319–325; 235/151.3; 364/498

[56] References Cited

U.S. PATENT DOCUMENTS

| 3,646,331 | 2/1972 | Lord ........................ 356/96 X |
| 3,734,621 | 5/1973 | Moody et al. ................ 356/97 |

FOREIGN PATENT DOCUMENTS 1074810 7/1967 United Kingdom ............... 356/229

*Primary Examiner*—F. L. Evans
*Attorney, Agent, or Firm*—Stanley Z. Cole; William A. Knoeller; Gerald M. Fisher

[57] ABSTRACT

In a scanning spectrophotometer, in which a narrow wavelength band of radiation can be selected from a range of wavelengths for transmission alternately through a sample cell and a reference cell, continuous automatic baseline correction is provided. A pulse train signal is generated, wherein the number of pulses represents the ratio of a parameter (e.g., intensity) of the radiation transmitted, respectively, through the sample and reference cells. A ratio of unity represents the baseline, and deviations from the baseline are indicated by changes in the number of pulses in the pulse train. Digital information indicative of baseline deviations is stored in a memory device when the spectrophotometer is being calibrated, and is retrieved from the memory device during operation of the instrument for sample analysis. The retrieved information generates a correction signal, which provides a continuous baseline correction.

4 Claims, 2 Drawing Figures

SPECTROPHOTOMETER

This is a continuation of copending patent application Ser. No. 626,599 filed on Oct. 28, 1975, which was a continuation-in-part of patent applications Ser. No. 424,400 filed on Dec. 13, 1973 and Ser. No. 594,902 filed on July 10, 1975, all now abandoned. Priority is claimed based upon Australian patent application No. PB 1691 filed Dec. 20, 1972.

The invention relates to spectrophotometers as used in the analytic determination of elements and molecular species and is applicable to Ultra-Violet, Visible and Infra-Red spectrophotometers. As a matter of convenience, however, the invention will be hereinafter described in relation to UV-Visible spectrophotometers and, more specifically, to a scanning double beam UV-Visible spectrophotometer.

The advantages of double beaming in spectrophotometers is well known as a means of drastically reducing errors in analysis (whilst scanning through a range of wavelengths) by compensating for such variables as source intensity, detector spectral response, optical component transmission, etc., with variation in wavelength. There remains in a double beam system, however, the problem of lesser wavelength dependant errors resulting from such variables as optical mismatch between sample and reference beams, non-uniform optical degradation, non-coincidence of sample and reference beams on an inhomogeneous detector surface, etc., and, to a substantially greater extent, the introduction of certain accessories (such as an integrating sphere) into the sample compartment which can produce gross errors that have to be accounted for in the final analysis.

These errors may be observed by setting the spectrophotometer to a datum output signal (say 100% transmission) with identical standards in both sample and reference beams (in the sample compartment) and scanning through the wavelength range of interest. The resultant chart recorder output will show the deviations from the chosen datum. This result is termed the "baseline" of the instrument. Specifications on most good quality instruments at this time guarantee deviations of less than ±1% on installation. It remains, however, that in order to obtain $<\pm 1\%$ deviation throughout production quantities, time consuming tests and set-up procedures must be undertaken and further, to maintain $<\pm 1\%$ deviation throughout the life of the instrument periodic calls must be made upon users when the need arises to reset and recalibrate the baseline.

It is a principal object of the present invention to provide a scanning double beam UV-Visible spectrophotometer having a means whereby the baseline is continuously corrected automatically within pre-determined scan limits set by the operator. The operator may select any one of a number of chart recorder/wavelength scan limits and, by "running" a baseline check as described above, may store a "fingerprint" of that baseline in digital form such that with any subsequent sample analysis performed within that selected range the stored digital information is retrieved in synchronism with the scan, re-converted into analog form and is used to correctly offset the analog source from which it was first derived, thus correcting any baseline deviations throughout the analysis. The invention is unique in:

1. the method of taking baseline deviations as a voltage offset to the datum reference voltage, storing these deviations digitally and converting back to an analog form of offset applied to the originating amplifier;
2. the use of variable scan range which, regardless of its limits, uses the complete storage capacity of the digital store to fingerprint the baseline. This allows for a very wide range of correction resolution;
3. the method of storing and retrieval allows for much larger baseline deviations than prior art owing to the gross baseline modifications contemplated by the addition of aforementioned accessories in the sample compartment.

In a double-beam spectrophotometer, to which the invention is especially applicable, the light source beam is split into two paths, and the resulting two beams are respectively passed through a sample cell and a reference cell. It is preferable to combine the resulting two beams into one path which is incidented upon the detector, so that the two sources of that incident beam are displaced in time to permit comparison of the intensity of those two sources. It is also preferred that means is provided to intermittently block the passages of the incident beam to the detector so that the detector receives information regarding the light through the reference cell, the sample cell and during darkness. The detector converts these three light signals into three electronic signals (displaced in time) whose amplitudes are proportional to the amount of light incident upon the detector. The three signals are then separated electronically and steered into separate paths. The dark or "zero" signal is a measure of "dark current" from the detector and is used to offset a pre-amplifier of the instrument to maintain a stable zero as a signal datum, and the reference signal is compared against a highly stable reference voltage which is pre-set to a value equivalent to a reference signal amplitude produced by the detector due to 100% transmission through the reference cell. Any difference occurring due to imbalance in these two levels is fed back to the detector to automatically adjust the detector gain to regain balance between the reference voltage and the reference cell signal. The sample signal is then processed and amplified, the resulting output of the signal amplifier being a voltage, the amplitude of which is the ratio of percent transmission through the sample cell ($T_s$) to that through the reference cell ($T_R$), i.e., $T_S/T_R$. This result is then applied to a recording device such as an XY Recorder.

The invention will be hereinafter described in greater detail in relation to a double beam UV-Visible spectrophotometer, but it is to be appreciated that the invention is also applicable to spectrophotometers of the single beam type, and to Infra Red spectrophotometers.

The following description refers in more detail to these essential features and further optional features of the invention. To facilitate an understanding of the invention, reference is made to the accompanying drawings where these features are illustrated in preferred form. It is to be understood however, that the essential and optional features of the invention are not limited to the specific forms of these features as shown in the drawings.

Figure 2:
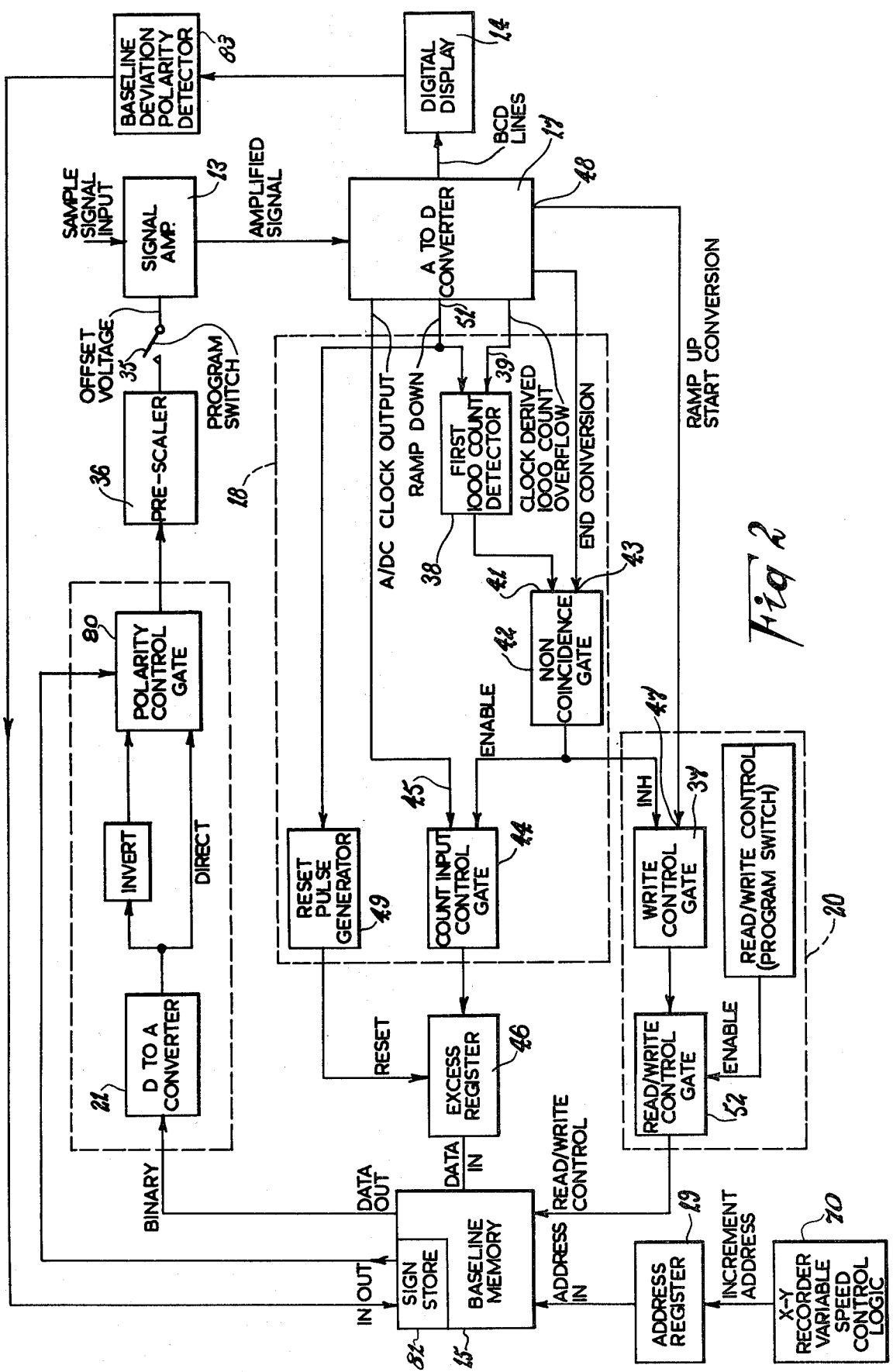

In the drawings:

FIG. 1 is a block circuit diagram of an example embodiment of the invention; and FIG. 2 is a block circuit diagram showing the baseline compensator of FIG. 1, in greater detail.

A typical double-beam UV-Visible spectrophotometer to which the invention is applicable is shown diagrammatically in FIG. 1 of the drawings, and includes a light source 2, which is selectable according to whether the apparatus is to be used in the ultra-violet or visible light range, and is arranged to direct a beam of light 4 into a monochromator scan assembly 3. The assembly 3 includes a movable grating or prism or other wavelength selector operatively connected to a suitable drive 5, and is tuned to select a discrete wavelength from the beam 4, excluding all other wavelengths. A chopper device 6 is positioned to receive the light beam from the monochromator 3, and is operable to split the incident radiation into two paths which pass through a reference cell 7 and a sample cell 8 respectively. The chopper device 6 typically comprises a rotating mirror, the rotation of which is mechanically correlated with the rotation of the beam combiner 9 by a synchronization control device 50. The resulting two beams, after passing through their respective cells, are received by a beam recombiner 9 which functions to direct those beams along the same path to a detector unit 11. The reference and sample cell beams are out of phase (displaced in time) in their transmission to the detector unit 11, and when they reach that unit, they each contain information regarding the light through the respective cells. The detector unit 11 converts those light signals into electronic signals (displaced in time) whose amplitudes are proportional to the amount of light incident upon the detector 11. The detector 11 is supplied by a stable voltage source 51, which in FIG. 1 is shown to be stabilized with respect to the output of a reference voltage generator 52 by an automatic gain control device 53. The output of the detector 11, which will be hereinafter described, is transmitted to a recorder 10 and to a read-out digital display 14. The signal to the recorder 10 is first amplified by a Y axis control device 56, in order to adapt the signal to a scale appropriate to the dependent variable input receivable by the recorder 10. In transmission to both the recorder 10 and the digital display 14, the output signal of the detector 11 passes through a pre-amplifier 12 and a signal amplifier 13, which function in a known manner. The processing of the output signal from the detector 11 by the pre-amplifier 12 includes a zero offset correction provided by a zero stability control device 55, which is correlated with the time dependence of the radiation flux incident upon the detector by an electronic signal from the synchronization control device 50.

The reference and sample cells, 7 and 8 respectively, are included within an optical system which needs to be adjusted with extreme accuracy to ensure minimum deviation of the baseline. Prior to the present invention, it was generally accepted that high quality instruments could be expected to have a baseline deviation better than 1% transmission (T)—i.e., when the instrument is programmed in the "transmission" mode. The baseline may be also measured in absorbance units when the instrument is programmed in the "absorbance" mode, and absorbance is measured as a logarithmic function of %T. When quoted in absorbance units, the aforementioned deviation in baseline is approximately plus or minus 0.005 absorbance units at zero absorbance. It will be convenient to describe the invention in relation to "transmission" mode programming.

A typical instrument as described above and modified to incorporate the invention is shown diagrammatically in FIG. 1 of the drawings, and includes a storage unit (baseline memory) 15 having the ability to store information fed to it electronically, and the further ability to permit retrieval of that information without destruction of "memory". The instrument also includes an analog-to-digital (A/D) converter 17 which receives signals from the detector unit 11 and is operative to convert those signals into a form suitable for receipt and storage within the storage unit 15, and address control means 16 which is operative to ensure that a particular wavelength signal is addressed to a selected component of the memory unit 15. Selector means including a read/write control 20 is operable to convert the memory unit 15 from a storage operation (write mode) to a retrieval operation (read mode), and in each mode the spectrophotometer is operative to scan through the full range of operative wavelengths, and the address control means 16 functions to address each particular wavelength signal to the correct component of the store.

The memory unit 15 may take any one of several forms, but preferably comprises a plurality of discrete memory elements or chips, each being adapted to retain a large number of items of information in digital form. According to one particular embodiment, each memory element is a metal oxide silicon chip containing a large number of binary bits, but other suitable semiconductor elements may be used, or each element may be a ferrite core type material or any other type of digital storage device.

In an example arrangement, 9 memory chips are provided, and each contains 256 binary bits arranged as a $256 \times 1$ matrix. 8 of the chips are used for numerical baseline error data, and the 9th is a "sign" store to indicate whether the error is above or below the set reference level. The use of 8 chips for data storage affords a maximum of 255 decimal units of data acquisition, i.e., up to 25.5%T if programmed in "transmission" mode, or 0.255 absorbance units (A) if programmed in the "absorbance" mode. The inclusion of a "sign" store doubles the range to plus or minus 25.5%T or plus or minus 0.255A respectively. If further memory or data chips are employed, the storage range will be further extended.

The memory unit 15 provides a "finger-print" of the baseline characteristics existing under any particular set of circumstances, and is programmed by the operator of the instrument. A baseline reference equivalent to 100%T is established by reference to a predetermined voltage, and the baseline characteristics existing under the prevailing operating conditions are a function of the differences between that voltage (represented in digital form) and signals received from the detector unit 11 of the instrument. The aforementioned signals are representative of the conditions existing within the optical system of the instrument, and are produced in a known manner through a photo-multiplier tube or other suitable means. It will be appreciated that the "fingerprint" is established without a sample in the sample cell 8, or with similar standards in each cell, so that there is "full" transmission of the sample beam.

In the diagrammatically illustrated example instrument according to the invention, the intensity of the light beam received by the detector unit 11 is converted into an output voltage of that unit, and the A/D converter 17 responds to that output voltage to produce a series of pulses i.e., a pulse train), the duration of which (i.e., number of pulses in the train) is proportional to the output voltage, and that pulse series of course represents a baseline signal. The A/D converter 17 may be a conventional dual ramp analog-to-digital converter having its own clock and outputs to indicate:

(a) Each 1000 counts.
(b) Duration of the Up Ramp.
(c) Duration of Down Ramp.
(d) End of Conversion Cycle (Transfer).
(e) Baseline compensation data lines to connect the digital display 14.

The A/D converter 17 is adjusted such that an analog input from the signal amplifier 13 representing 100%T will convert to 1000 counts during the Down Ramp.

Difference detection means 18 is provided to determine the difference between the baseline signal emanating from the A/D converter and the digital value of the preset baseline reference voltage, and relay that difference to the memory unit 15. The difference detection means 18 will be hereinafter described in detail in relation to operation of the instrument.

Address control means 16 is also provided to ensure that information from the difference detection means 18 is fed to the correct part of the storage unit 15. The address control means 16 is operatively connected with the storage unit 15 through a suitable address register 19. The address register 19 in the preferred embodiment includes two digital store devices, which act as an 8-bit store, and which determine in which byte of the storage unit 15 information is to be stored, or from which byte information is to be retrieved, as the case may be.

In the address control means 16 shown in FIG. 1, a master clock 31 controls both the monochromator 3 and recorder 10 scan speeds. To control the speed of the monochromator 3, timing pulses from the clock 31 are processed by a variable speed control logic device 60, the output of which is further processed by a scan control logic device 61, to instruct the monochromator scan drive 5. Similarly, to control the speed of the recorder 10, timing pulses from the clock 31 are processed by a variable speed control logic device 70, which bears a relationship to the recorder 10 that is analogous to the relationship between the logic device 60 and the monochromator 3. A selectable scan range control 32 selects the range of wavelengths over which the monochromator 3 is required to scan and determines the speed at which the recorder 10 must travel to cover the selected range across its full X axis. Both the recorder 10 and the monochromator 3 are digitally controlled.

The address register 19 is incremented by a recorder speed control 33 forming part of the control means 16, such that pulses to the recorder 10 increment both the recorder X axis travel through a drive 34, and the address register 19. The number of increments for full X axis travel on all ranges is proportional to the number of locations used in memory. Thus, regardless of the wavelength range selected, the recorder 10 will use its full X axis travel and the baseline memory will always be used to capacity. This means that when a new wavelength range is selected a new program must be run for that range.

Consideration will now be given to operation of the instrument, and it will be convenient to refer more particularly to FIG. 2 of the drawings which provides greater detail of the difference detector 18. Before commencing a baseline calibration run, the program switch 35 is made such that the baseline memory 15 is in the WRITE mode (i.e. read/write control 20 is enabled) and the connection between the pre-scaler 36 and the signal amplifier 13 is broken.

The output from the signal amplifier 13 is applied to the A/D converter 17 and the commencement of the Up Ramp is the start of conversion. This is sensed by the write control gate 37 of the read/write control 20, and enables the data present at the "Data In" terminals of the baseline memory 15 to be written into memory at the address currently held in the address register 15.

At the end of the Up Ramp, the Down Ramp commences. The duration of Down Ramp is proportional to the number of counts produced by the A/D converter 17 for a given analog input, thus for an input equivalent to 100%T the A/D converter 17 produces 1000 counts and the duration of the Down Ramp is proportional to 1000 counts. Referring in particular to FIG. 2, the start of the Down Ramp is sensed by a 1000 count detector 38, which has a second input 39 from the 1000 count output of the A/D converter 17. The count detector 38 is arranged to detect the occurrence of the first 1000 count overflow pulse after commencement of Down Ramp and to output a signal which is then fed to an input 41 of a non-coincidence gate 42 whose function is to output a signal only at times when its inputs 41 and 43 are dissimilar. The input 43 is derived from the "End of Conversion" signal from the A/D converter 17. The output of the non-coincidence gate 42 is thus a pulse whose duration is the time difference between the first 1000 count output occurring and the completion of conversion of the signal presented to the input of the A/D converter 17. The output of the non-coincidence gate 42 is used, firstly, to enable a count input control gate 44 and, secondly, to inhibit the write control gate 37.

The count input control gate 44 has a second input 45 which is derived from the clock of the A/D converter 17 so that the output of the gate 44 is a train of pulses at the clock frequency for the period determined by the output pulse of the gate 42. Since this period is the difference in time between the first 1000 count and the end conversion, then the number of pulses appearing at the gate 44 is equal to the deviation above or below 1000 counts or the A/D conversion of the analog deviation from 100% transmission presented at the input of the A/D converter 17. The pulses are stored in an excess register 46 as data input to the baseline memory 15. At the conclusion of the Enable pulse from the gate 42, further counts are inhibited and the write control gate 37 is enabled.

At the commencement of the next cycle Ramp Up, a second input 47 of the write control gate 37 receives a pulse from the Ramp Up output 48 of the A/D converter 17 and writes the data stored in the excess register 46 into memory at the address contained in the address register 19.

At the commencement of the next Ramp Down, the excess register 46 receives a re-set pulse and is set to zero via a re-set pulse generator 49 which is controlled by the Ramp Down output 51 of the A/D converter 17.

The above operation is then repeated at each memory address register increment.

The digital display 14 is connected to the A/D converter 17 so that decimal readout is available. In a preferred arrangement, for a 100% transmission input signal the digital display 14 will indicate 100.0 which is equivalent to 1000 counts. The most significant digit (MSD) of this display is used to detect whether the binary figure contained in the excess register 46 (the deviation from 100% transmission) is above or below 100%. Detection of the MSD and the supply of an appropriate polarity signal to sign store 81 is accomplished by the baseline deviation polarity detector 83. Thus, if the MSD is decimal 1, then the baseline is equal to or greater than 100% and the sign stored in the baseline memory sign store 81 by detector 83 is negative, signifying that the quantity stored at that location (wavelength) must be subtracted in order to correct the baseline to 100% transmission. If, however, the MSD is a decimal 0 then the deviation is less than 100% transmission, the sign stored in the BM sign store by detector 83 is positive, signifying that the quantity stored at that location must be added in order to restore the baseline to 100% transmission.

On completion of the full selected scan, the program switch 35 is set so that for subsequent scans over the selected range the baseline memory 15 may read out its stored information to restore the baseline throughout the range to 100% transmission. Thus, the program switch 35 disables the "Write Mode" and Enables the "Read Mode" via a read/write control gate 52 and connects the output of the pre-scaler 36 to the signal amplifier 13.

Consideration will now be given to operation of the instrument during analysis of a sample.

At the start of scan, the address register 19 is re-set to zero. As the range of wavelengths is scanned, the data previously written in to baseline memory 15 appears at the data outputs (coincident with each address increment) in the same form as it was written-in, i.e. binary words. These words are applied to a digital-to-analog converter 21 which converts each word into an analog voltage level depending upon the "weight" of the binary word.

The output from the D/A converter 21 is then applied to the pre-scaler 36 which adjusts the voltage to a value which, when supplied as an offset to the signal amplifier 13 from which it was first derived, will maintain a constant baseline. The direct and inverted outputs of the D/A converter 21 are selectably available as inputs to the pre-scaler 36, via a polarity control gate 80, in accordance with the content of the sign storage portion 81 of the baseline memory unit 15. Thus, as the wavelength range is scanned, the baseline variations that occurred and were stored at each wavelength increment during programming are added to or subtracted from all new incoming signals at these wavelengths to compensate for errors due to deviation.

The current instrument utilises a four full digit A/D converter which limits the correction and hence the baseline deviation to 0.1%. This, however, could be increased by simply adding more digit capacity to the A/D converter 17. Due to limitations in the analog circuitry, however, the addition of more A/D converter capacity may be of little advantage. The storage capacity used in an example arrangement is 256×8 bit bytes for data and 256×1 bit bytes for sign. This may advantageously be increased to any required extent for improved wavelength increment and hence baseline resolution, however, limitation is placed on the speed of D/A conversion in present state-of-the-art D/A conversion devices.

It has been found that an instrument as described improves the accuracy of measurement by substantially decreasing baseline deviation, and such as instrument avoids time consuming adjustments after a change in the conditions of operation. The baseline correction is automatic during use, so that the instrument is simple to operate.

The instrument described is capable of restoring baselines having deviations up to as much as 25.6% from the datum, i.e. from 125.6% to 74.4%. Baseline modifications of this order have been observed with the introduction of aforementioned accessories into the sample compartment.

Finally, it is to be understood that various alterations, modifications and/or additions may be introduced into the constructions and arrangements of parts previously described without departing from the spirit or ambit of the invention as defined by the appended claims.

Having now described our invention, what we claim as new and desire to secure by Letters Patent is:

1. A spectrophotometer comprising:
    means for generating a beam of electromagnetic radiation, said beam comprising a range of wavelengths of said radiation;
    wavelength selector means disposed in the path of said beam for providing transmission of a narrow wavelength band within said range of wavelengths of said radiation;
    means connected to said wavelength selector means for causing said wavelength selector means to scan continuously through said range of wavelengths, whereby sequential transmission of different narrow wavelength bands of said radiation can be provided;
    chopper means disposed to receive any one of said narrow wavelength bands of radiation, and being operative to direct said one narrow wavelength band of radiation alternately through a reference cell and a sample cell;
    signal generating means disposed to receive radiation that has been transmitted through said reference and sample cells, said signal generating means being responsive to said transmitted radiation to produce a pulse train signal, the number of pulses in said pulse train being representative of the ratio of the intensities of the radiation transmitted, respectively, through said reference and sample cells, said signal generating means also producing a first signal representing when a number of pulses in said pulse train corresponding to a unity ratio is achieved and a second signal representing the end of said pulse train;
    difference detection means responsive to the occurrence of said first and second signals for determining deviations from unity for the ratio represented by the number of pulses in said pulse train;
    storage means operable in a calibration mode to store information characteristic of any deviations from unity for said ratio detected by said difference detection means, and operable during a sample analysis mode to retrieve said stored information; and
    correcting means operatively connected to both said storage means and said signal generating means so as to produce a correction signal characteristic of said stored information when radiation is being transmitted through said sample cell, and to apply said correction signal to said signal generating means to modify said pulse train signal so that said pulse train signal, as so modified by said correction signal, is representative of the effect of material in said sample cell on the intensity of said radiation.

2. The spectrophotometer of claim 1 wherein said means for causing said wavelength selector means to scan through said range of wavelengths is operatively connected to said storage means so that each item of said information corresponds to a particular wavelength in said range of wavelengths.

3. The spectrophotometer of claim 1 wherein a means is provided for converting said retrieved information into an analog signal, and wherein a phase invertor responsive to said analog signal generates said correction signal.

4. The spectrophotometer of claim 3 wherein said correcting means further comprises a switching means that functions to apply said correction signal to said signal generating means during said sample analysis mode, thereby producing a continuously corrected intensity indicative signal.

* * * * *